(12) United States Patent
Utku et al.

(10) Patent No.: US 9,827,261 B2
(45) Date of Patent: Nov. 28, 2017

(54) ETOPOSIDE AND PRODRUGS THEREOF FOR USE IN TARGETING CANCER STEM CELLS

(71) Applicant: CELLACT PHARMA GMBH, Dortmund (DE)

(72) Inventors: Nalan Utku, Dortmund (DE); Steven R. Gullans, Natick, MA (US)

(73) Assignee: CELLACT PHARMA GMBH, Dortmund (DE)

( * ) Notice: Subject to any disclaimer, the term of this patent is extended or adjusted under 35 U.S.C. 154(b) by 0 days.

(21) Appl. No.: 14/775,707

(22) PCT Filed: Mar. 12, 2014

(86) PCT No.: PCT/EP2014/054785
§ 371 (c)(1),
(2) Date: Sep. 13, 2015

(87) PCT Pub. No.: WO2014/140072
PCT Pub. Date: Sep. 18, 2014

(65) Prior Publication Data
US 2016/0022721 A1 Jan. 28, 2016

(30) Foreign Application Priority Data
Mar. 12, 2013 (GB) .................................. 1304417.7

(51) Int. Cl.
*A61K 31/7048* (2006.01)
*A61K 45/06* (2006.01)

(52) U.S. Cl.
CPC .......... *A61K 31/7048* (2013.01); *A61K 45/06* (2013.01)

(58) Field of Classification Search
None
See application file for complete search history.

(56) References Cited

U.S. PATENT DOCUMENTS

2010/0298352 A1   11/2010   Prochownik et al.

FOREIGN PATENT DOCUMENTS

| EP | 2 385 370 A1 | 9/2011 | |
| EP | 2385370 | * 11/2011 | ......... G01N 33/5011 |
| WO | WO 03/048166 A1 | 6/2003 | |
| WO | WO2011/127948 | * 10/2011 | ........... A61K 31/704 |
| WO | WO 2011/127948 A1 | 10/2011 | |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Sampieri et al., Seminars in Cancer Biology, 22, 2012, 187-193.*
Jin, Feng et al., "Influence of Etoposide on anti-apoptotic and multidrug resistance-associated protein genes in CD133 positive U251 glioblastoma stem-like cells," *Brain Research*, 2010, 1336:103-111.
Wrasidlo, Wolf et al., "Synthesis, Hydrolytic Activation and Cytotoxicity of Etoposide Prodrugs," *Bioorganic & Medicinal Chemistry Letters*, 2002, 12(4):557-560.

* cited by examiner

*Primary Examiner* — Traviss C McIntosh, III
(74) *Attorney, Agent, or Firm* — Saliwanchik, Lloyd & Eisenschenk

(57) ABSTRACT

The present invention pertains to the use of podophyllotox in derivatives, such as CAP7.1, in methods for inhibition of and/or prevention of the growth and/or survival of cancer stem cells. The invention discloses the surprisingly specific activity of the compounds in accordance with the invention against a cancer stem cell population. In this respect the present invention provides the use of the compounds as described in the treatment of cancer, specifically of cancers which have a high risk of developing metastases, chemotherapeutic resistances and/or cancer relapse. Provided are novel methods of cancer treatment, and pharmaceutical compositions comprising the compounds as described, for use in such treatment methods.

9 Claims, 1 Drawing Sheet

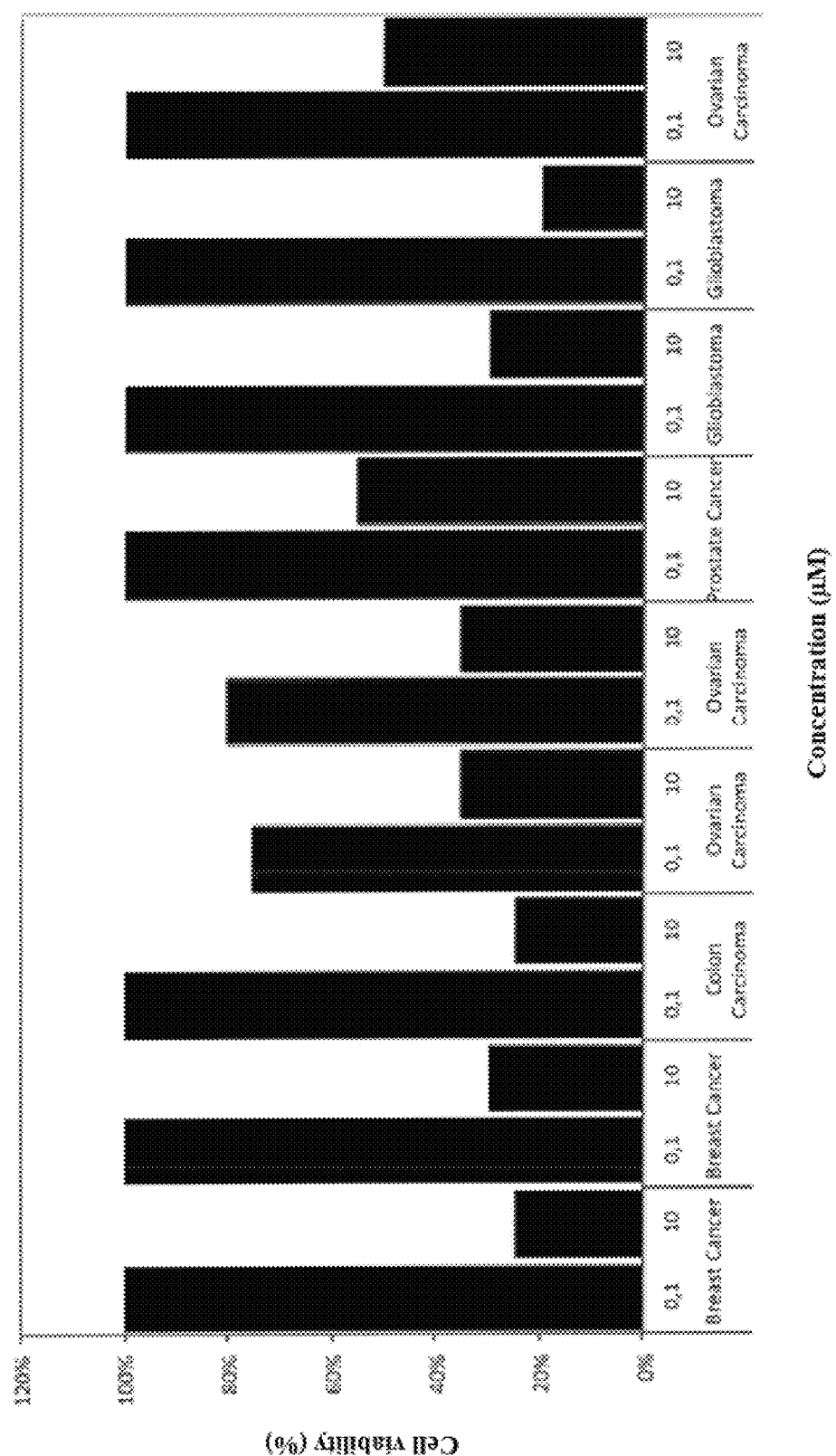

ETOPOSIDE AND PRODRUGS THEREOF FOR USE IN TARGETING CANCER STEM CELLS

CROSS REFERENCE TO RELATED APPLICATIONS

This application is a National Stage Application of International Application Number PCT/EP2014/054785, filed Mar. 12, 2014; which claims priority to Great Britain Application No. 1304417.7, filed Mar. 12, 2013; both of which are incorporated herein by reference in their entirety.

FIELD OF THE INVENTION

The present invention pertains to the use of podophyllotoxin derivatives, such as CAP7.1, in methods for inhibition of and/or prevention of the growth and/or survival of cancer stem cells (CSC). The invention discloses the surprisingly specific activity of the compounds in accordance with the invention against a cancer stem cell population. In this respect the present invention provides the use of the compounds as described in the treatment of cancer, specifically of cancers which have a high risk of developing metastases, chemotherapeutic resistances and/or cancer relapse. Provided are novel methods of cancer treatment, and pharmaceutical compositions comprising the compounds as described, for use in such treatment methods.

DESCRIPTION

Despite the huge breakthroughs in cancer treatment over the past few decades, cancer remains one of the most common causes of death. Cancers become resistant to treatment, or patients relapse following treatment. When relapsing, recurrent cancer cells often develop mutations which render the new tumor resistant against many forms of treatment like chemo therapy, for example by the expression of cellular membrane transporting proteins which allow the cancer cells to remove the chemotherapeutic agent from the cellular body before it can kill the tumorous cell. Furthermore, in patients treated with a chemotherapeutic, a continuous selection pressure exists to develop cancer cell clones which are resistant to the chemotherapeutic used. Extensive knowledge exists for example of various mutant forms of leukemia which develop during treatment with the tyrosine kinase inhibitor Imatinib. Imatinib binds to the Bcr-Abl kinase and mediates thereby cancer cell death. Although knowledge about cancer relapse is important for successful cancer therapy, it is especially difficult to study cancer relapse since the usually used animal models of cancer, like for example mice, do not provide a sufficiently long life span to acquire data on recurrent cancer cells.

Studies of neoplastic tissues have suggested the presence of self-renewing, stem-like cells within tumors known as cancer stem cells. These make up a minority of neoplastic cells within the tumor, and one of their defining characteristics is that they can 'seed' new tumors. Because of this, they are also known as tumor-initiating cells. In general, these cancer stem cells share common characteristics including the ability for self-renewal, induction of new tumors at low cell numbers, ability to produce tumors with a differentiated and heterogeneous cell profile, low rates of cell division and expression profiles which significantly differ compared to their differentiated counterparts. It is thought that cancer stem cells develop from healthy adult stem cells. Since cancer stem cells are long-living they have to be exposed much longer to mutagens in order to become transformed into a cancer stem cell.

Cancer stem cells may generate new tumors through the stem cell processes of self-renewal and differentiation into multiple cell types. Such cells are proposed to persist in tumors as a distinct population and cause relapse and metastasis by giving rise to new tumors. Therefore, since standard treatments in cancer therapy merely target the differentiated bulk of tumor cells, unfortunately what looks like a successful treatment is often only the reduction of tumor mass without killing the cancer stem cells which after the treatment is terminated may induce new tumors or metastasis. Cancer stem cells are thus responsible for a cancer relapse. Studies have indicated that primary and secondary tumors are composed up to 1 to 10% of cancer stem cells.

Invasive neoplastic cells drive cancer, and these include subpopulations of cancer stem cells. Many cancers metastasize to distant sites, and this leads to poor outcomes for morbidity and mortality—more than 90% of cancer deaths are as a result of metastases. Circulating tumor cancer stem cells, including tumor stem cells move around the body, 'seeding' new tumors. There is preclinical evidence to support this—in a mouse model, cancer stem cells and other cancer cells from head and neck squamous cell carcinoma (HNSCC) were injected into the tail veins of mice. The cancer stem cells migrated through the body and formed lung lesions, whereas the other cells did not. The epithelial-mesenchymal transition (EMT) is a step that is important in embryogenesis, and seems to be activated during cancer invasion and metastasis. Mani et al. induced this transition in immortalized human mammary epithelial cells (HMLEs), and these cells showed mesenchymal traits and expressed stem cell markers. The EMT may be involved in the invasion-metastasis cascade and could help the formation of macroscopic metastases, as well as increasing the number of self-renewing cells that can initiate the seeding of mammospheres which are enriched in stem cells.

Cancer stem cells have been linked with resistance to treatment, including both chemo- and radiotherapy. Stem cell populations are heterogeneous, and cancer treatments that do not destroy the entire stem cell population drive disease resistance by allowing more aggressive cells to proliferate. Stem cells may be less sensitive to chemotherapy and radiotherapy, so standard treatments enrich the stem cell population, increasing the resistance of the cancer. In support of this, HNSCC cells expressing c-Met are resistant to cisplatin treatment, and this seems to be mediated by their self-renewal pathways. In patients with colorectal cancer, cells that express the ATP-binding cassette member B5 (ABCB5) are likely to be resistant to fluorouracil (5-FU)-based chemoradiation therapy.

In a study of glioblastoma multiforme cell lines, radiation treatment enriched the concentration of stem cell-like cells. In a study of patients with cancer, the proportion of stem cell-like cells in the tumors was higher after chemotherapy (around 4.7% of the tumor, compared with around 13.6%), suggesting that the chemotherapy has eradicated the vulnerable cells, and the remaining cells are resistant to chemotherapy.

Etoposide is a chemotherapeutic drug derived from podophyllotoxin and acts as an inhibitor of topoisomerase II. The enzyme topoisomerase II induces transient DNA double strand breaks to enable modifications of DNA tertiary structure. Etoposide acts as a topoisomerase II poison leading to a stabilization of the cleavable complex, resulting in multiple non-repairable double strand breaks. There are two isoforms of topoisomerase II, alpha and beta. Expression of topoisomerase II alpha is regulated with the cell cycle, with a gradual increase starting in the G1 phase that peaks in G2/M, whereas in quiescent cells or terminally differentiated cells topoisomerase II is extremely underregulated. The action of etoposide is cell cycle dependent with maximal activity during the G2-S phase.

Etoposide is an important anti-tumour drug and is commonly used against a number of diverse tumours, for example pediatric cancers including lymphatic lymphomas, rhabdomyosarcomas and neuroblastomas. Etoposide is also used in the treatment of many common cancers in adults. It is the first line therapy in a series of tumours, e.g. small cell lung cancer, diffuse large cell lymphoma, testicular germ cell tumour (testicular cancer) and Hodgkin lymphoma. Etoposide is also active in e.g. Non-Hodgkin lymphoma, AIDS-related Kaposi's sarcoma, bladder cancer, Ewing sarcoma, brain tumours and ovarian germ cell tumours. However, there are factors limiting the applicability of etoposide, such as poor water solubility, metabolic inactivation, toxicity with side effects such as leucopenia and neutropenia and the resistance against etoposide developing in the treated patients.

WO 03/048166 pertains to the problem of providing pro-drugs of etoposide. Disclosed are pro-drugs of podophyllotoxins which substantially reduce adverse reactions when administered to a patient, that are stable in aqueous solutions, yet do not require the application of catalytic antibodies for their conversation into the active drug and which allow for a slow release of the drug at the intended side of action, i.e. a tumor.

WO 2011/127948 and WO/2011/128115 disclose the analogues of etoposide of WO 03/048166, in particular a compound known as CAP7.1, which are suitable for treating drug-resistant (e.g. etoposide-resistant) tumors, especially multidrug-resistant tumors and thus are able to overcome drug (e.g. etoposide) resistance and particularly multidrug resistance. Patients having a tumor that has a multidrug-resistant phenotype mediated by the multi-drug resistance transporter protein MDR-1 are disclosed to be treatable by the described analogues of etoposide. This means that MDR-1 is expressed to such an extent that the tumor or certain cells of the tumor display(s) a multidrug-resistant phenotype, i.e. the response to certain drugs (compounds, chemotherapeutic agents) is impaired.

Metformin, a standard drug administered to patients suffering from diabetes was shown to be an effective compound to inhibit the cellular transformation and to selectively kill cancer stem cells in four genetically different types of breast cancer. In combination with the chemotherapeutic drug doxorubicin, metformin could reduce tumor mass and prevent cancer relapse more effectively than either of the drugs alone (Hirsch H A et al., Cancer Res 2009).

A screen for agents that specifically kill cancer stem cells was performed by Gupta and colleagues. Their approach could overcome the problem of low cell numbers of cancer stem cells that before made high throughput screening almost impossible. The study applied epithelial mesenchymal transition (EMT) in order to generate a sufficiently large population of cancer stem cells and screened a compound library to find salinomycin to be a potential specific and selective killer of breast cancer stem cells (Gupta P B et al., Cell 2009).

WO 2011/116344 describes a method of killing cancer stem cells based on the level of expressed inhibitor of apoptosis (IAP) in the cancer stem cells. According to the disclosure of said literature, a low level of IAP in cancer stem cells indicates a sensitivity of these cells to a death receptor agonist. Thus, death receptor agonists could be used as a therapeutic to kill cancer stem cells in case they do not express IAP in sufficient amounts to block apoptosis.

Therefore, in view of the above described prior art, the object of the present invention is to develop novel specific therapies that target cancer stem cells. Such therapies hold hope for improvement of survival and quality of life of cancer patients, especially for sufferers of metastatic and/or relapsing disease.

In a first aspect of the present invention, the above objective is solved by an etoposide, or analogue of an etoposide, for use in a treatment comprising the inhibition of and/or prevention of the growth and/or survival of cancer stem cells.

Specifically preferred is an etoposide, or analogue of an etoposide, for use in a method for therapeutically destroying cancer stem cells. In a preferred embodiment thereof said cancer stem cells are (a) cancer stem cells resistant to chemotherapy or radiotherapy, or (b) potentially relapsing cancer stem cells.

In another aspect, the objective of the present invention is solved by a compound according to formula I,

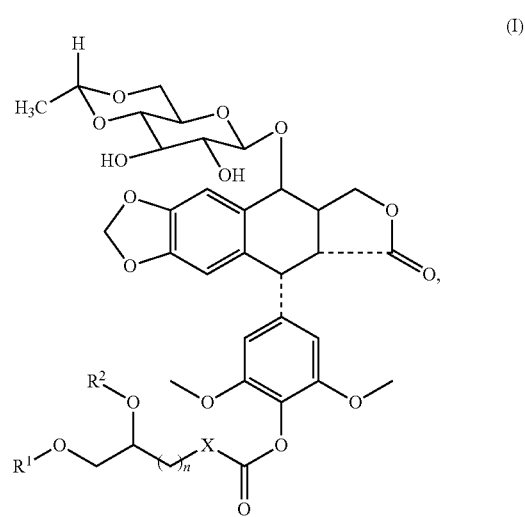

wherein X is selected from the group consisting of O, NH and S, n is 0, 1 or 2, and $R^1$ and $R^2$ are independently selected from the group consisting of H, methyl and ethyl, or together form a group $CR^3R^4$ wherein $R^3$ and $R^4$ are independently selected from the group consisting of H, methyl and ethyl, or a pro-drug, derivative solvate or salt there-of, for use in a treatment comprising the inhibition of and/or prevention of the growth and/or survival of cancer stem cells.

Preferably, the compound for use in a treatment comprising the inhibition of and/or prevention of the growth and/or survival of cancer stem cells including circulating tumor cells according to the invention is selected from the group consisting of

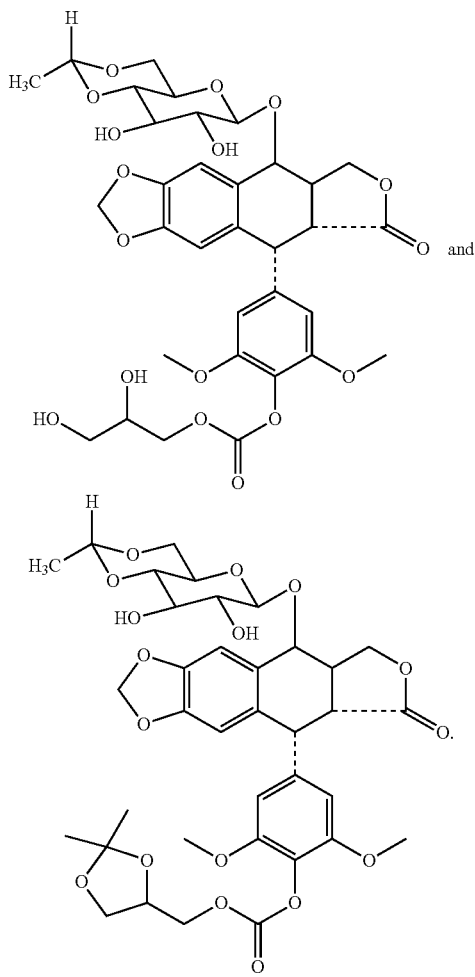

Preferably the compound of the present invention is CAP7.1.

Surprisingly it was discovered that the compounds provided by the present invention have the ability to inhibit/prevent the growth and/or survival of cancer stem cells. Treatment of various cancer stem cell lines with the above depicted compounds significantly reduced cancer stem cell numbers opposed to control experiments. These results indicate that the compounds provided by the present invention, as well as their derivatives, or salts and solvates thereof, are particular useful for treating a cancerous disease that is known to have a high probability of metastasizing, developing resistances to cancer therapy and/or of relapsing.

In this respect it is a preferred embodiment of the present invention that the compounds for use in a treatment, wherein the treatment comprises the inhibition of and/or prevention of the growth and/or survival of cancer stem cells, are used in a patient in need of such a treatment. Particularly it is preferred that said patient is suffering from a cancer disease, preferably a cancer disease characterized by the expression of at least one cancer stem cell marker, most preferably wherein said cancer disease is driven by the presence of cancer stem cells.

There are a number of biomarkers, including cell surface markers and changes in expression, that can be used to mark stem cells in a wide range of cancers of different origin—see Table 1. This list is not exhaustive, but indicates the breadth of markers that could be used as targets. Preferably, the compounds of the present invention are used in the treatment of a cancer that is characterized by the presence of cancer cells expressing at least one of the cancer stem cell marker provided in table 1. Preferably, the expression of said biomarker is significantly higher than the expression in a non cancer stem cell.

TABLE 1

| Tumour | Marker |
|---|---|
| Cancer stem cell biomarkers | |
| Acute or chronic myeloid leukaemia | CD34+, CD38−, CD123+, CD34+/CD38−/CD123+ |
| Bone sarcoma | Stro-1+, CD105+CD44+ |
| Brain carcinoma | CD133+, nestin+, GFAP−, β-tubulin− |
| Breast carcinoma | CD44+CD24−/lowlineage−, Oct3+, Oct4+, Cx43 |
| CNS | CD133+ |
| Colon | CD133+, CD166+, CD44+, CD29+, CD24+, Lgr5+, ABCB5+, CD26+ and nuclear-catenin |
| Glioma | CD133+, increased levels of angiogenic factors |
| Head and neck cancer | CD44+, c-Met, CD133+, ABCG2, ALDHhigh ALDH1 |
| Hepatocellular | CD133+ |
| Lung | CD133+, Sca-1+, CD45− |
| Medulloblastoma | CD133+, Hoechst 33342 dye exclusion, nestin+ |
| Melanoma | CD20+ |
| Multiple myeloma | CD138−, CD19+ |
| Pancreatic | CD133+ CXCR4+ |
| Prostate carcinoma | CD44+α2β1hi/CD133+, Sca-1+, CD44, CD24, epithelial-specific antigen |
| Renal | CD133+ [14] |
| Thyroid | Hoechst 33342 dye exclusion, CD133+, Oct4, ALDH-positive |

Based on 'Cancer Origins and Carcinogenesis'

Yet another preferred embodiment of the present invention pertains to the compounds in accordance with the present invention for use in a treatment as described herein, wherein the patient is suffering from a cancer disease selected from a chemo- or radiation therapy resistant cancer, a metastatic cancer, an aggressive cancer, a refractory cancer, a recurrent cancer or a non-resectable tumor. For example, but without being limited thereto said drug resistant cancer disease is characterized by a tumor expressing a protein of the multi-drug resistant ABC transporter type, preferably by a tumor having the MDR1 phenotype.

In particular preferred in the context of the herein described invention is that the compound for use in a treatment comprising the inhibition of and/or prevention of the growth and/or survival of cancer stem cells as described herein above, is used in a treatment wherein the patient is a cancer patient suffering from a cancer relapse. Thus, the compounds in accordance with the present invention are of particular use in a disease scenario wherein a cancer patient was already subjected to a cancer treatment of any kind, for example tumor resection, radiation therapy, chemotherapy or the like. However, the cancer cells in said treated patient could not be killed entirely in that treatment or the cancer was thought to have been sufficiently treated but subsequently reoccurred. Therefore, the present invention in a particularly preferred embodiment pertains to the use of the compounds disclosed herein—compounds of formula I—in a specified patient group which suffered from, or are expected to suffer from (having a high probability of developing), a cancer relapse, preferably wherein said patient group is further characterized in that they were subjected to a at least one unsuccessful cancer treatment.

One further embodiment then relates to the use of the compounds in accordance with the present invention in the treatment of a patient that is suffering from a cancer relapse as described above, and who is further suffering from a metastasizing cancer.

The term "metastasis" as used in this application includes local, regional and distant metastases. Local metastases are formed in the vicinity of the primary tumour, usually when malignant tumour cells are leak into the respective tissue, also across organ borders. Regional metastases are metastases present in draining lymph nodes, which are usually formed when tumour cells leak into the lymph vessels and localise in the respective lymph nodes (localised spread to regional lymph nodes near the primary tumour). Distant metastases are often formed when tumour cells leak into blood vessels; they are localised in organs distant from the organ of the primary tumour.

Thus, preferably the compound for use in a treatment comprising the inhibition of and/or prevention of the growth and/or survival of cancer stem cells in accordance with the invention, are used in a cancer therapy, wherein the tumor or cancer is selected from the group consisting of solid or hematopoietic tumors e.g adenocarcinoma, hypopharynx cancer, lung cancer, diffuse large cell lymphoma, Burkitt's lymphoma, Hodgkin lymphoma, Non-Hodgkin lymphoma, histiocytic lymphoma, lymphatic lymphoma, acute T-cell leukaemia, pre-B-acute lymphoblastic leukaemia, chronic and acure myeloitic leukemia, Gastrointestinal cancers eg. (gall bladder-, stomach-, esophageal-, pancreatic-, colon cancer, bile duct carcinoma) thymus carcinoma, urothelium carcinoma, testicular cancer, prostate cancer, bladder cancer, brain tumour, skin tumor including AIDS-related Kaposi's sarcoma, Ewing sarcoma, rhabdomyosarcoma, neuroblastoma, ovarian cancer, head and neck cancer, osteosarcoma, melanoma, breast cancer and CUP syndrome.

Preferred embodiments of the present invention pertain to uses/methods of the compounds of the invention in a treatment comprising the inhibition of and/or prevention of the growth and/or survival of cancer stem cells in accordance with the invention, are used in a cancer therapy, wherein the tumor or cancer is selected from the group consisting of breast cancer, colon carcinoma, ovarian carcinoma, prostate cancer, or glioblastoma.

In one preferred alternative or additional embodiment the cancer to be treated in accordance with the present invention is a cancer resistant to chemotherapy. In particular wherein the chemotherapeutic to which the cancer is resistant, preferably in the context of a cancer relapse, is selected from the group consisting of therapeutic antibodies and kinases, and respective chemotherapeutic drugs are preferably selected form the group consisting of alkylating agents, platinum-based agents, intercalating agents, antibiotics, inhibitors of mitosis, taxanes, inhibitors of topoisomerase and antimetabolites. In particular, the chemotherapeutic drug is selected from the group consisting of all-trans retinoic acid, azacitide, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, trofosfamide, valrubicin, vinblastine, vincristine, vindesine and vinorelbine.

Due to the surprising effect of the compounds in accordance with the present invention, the treatment is preferably a treatment that results in a reduction of tumor growth, preferably in cancer remission. Most preferably said treatment is characterized by the reduction of the number of cancer stem cells in a tumor of said patient, thereby preventing the patient from cancer relapse, resistances and/or the formation of metastasis.

Preferably, the treatment is at a daily dose as described in WO 2011/127948 and WO/2011/128115. Preferably, the treatment is at a daily dose of the compound of formula (I) of 120 mg/kg body weight (bw) or below. It has surprisingly been shown that the compounds of formula (I) due to their efficiency are active already in low concentrations, so that the daily dose can be lower than a corresponding dose of etoposide. More preferably, the daily dose of a compound of formula (I) is 100 mg/kg bw or below, even more preferably 80 mg/kg bw or below, still more preferably 50 mg/kg bw or below and most preferably 30 mg/kg bw or below.

In a preferred embodiment, the treatment comprises a first period of administration of a compound a formula (I) on a number of consecutive days (for example 4, 5, 6 or 7 days), followed by an intermittent period in which no compound of formula (I) is administered (the intermittent period lasting for example 1 to 4 weeks), followed by a second period of administration of a compound a formula (I) on a number of consecutive days (for example 4, 5, 6 or 7 days). Preferably, the first period of administration is 5 days, the second period of administration is 5 days and/or the intermittent period is 2 to 3 weeks.

Preferably, the treatment involves single dosage unit per day or in combination with other drugs.

The compounds of formula (I) are preferably administered by intravenous infusion. It has now been found that the compounds of formula (I) are enzymatically converted to the chemotherapeutic drug etoposide by carboxylesterases, in particular human carboxylesterases and especially CES1 and CES2. Carboxylesterases are present in a subset of tumours. For example, the publication Xu et al. (2002) Clinical Cancer Research 8, 2605-2611 shows that CES2 is expressed in 66% of the analysed human tumours (101 of 154), whereas it is expressed in 92% (55 of 60) of normal tissues.

It has been found that in mice with high levels of the corresponding carboxylesterases, the half life of CAP7.1 is very short, whereas it is longer in primates and in humans. The fact that CAP7.1 shows activity in mice in a xenograft model of MDR tumours suggests that CAP7.1 distributes early to the tumour sites. With respect to the fact that carboxylesterases cleave the compounds of formula (I) to etoposide, the compounds of formula (I) can be regarded as pro-drugs.

However, the compounds of formula (I) also have effects that are independent of their conversion to etoposide. Thus, they have a profile that can be differentiated from etoposide. For example, the compounds of formula (I) directly inhibit the MDR-1 gene product P-glycoprotein, in contrast to etoposide, which is ineffective on P-glycoprotein. Thus, P-glycoproteinmediated substrate efflux is reduced, which contributes to the effectiveness of the compounds of formula (I) on multidrug-resistant tumours and to the effect of overcoming multidrug resistance. Compounds of formula (I), e.g. CAP7.1, are not a substrate for P-glycoprotein. Etoposide is pumped out of the cells, whereas in contrast, compounds of formula (I), e.g. CAP7.1, remain in the cells for a longer period. This is indicative of the compounds of formula (I) inhibiting the activity of the pump (through direct binding to P-glycoprotein or mediated by binding to another protein). Thus, the concentration of the compounds of formula (I) inside tumour cells is higher than the concentration of etoposide. Compounds of formula (I) do not show cross-resistance with etoposide. In addition, the compounds of formula (I) remaining in the cells are able—in contrast to etoposide—to induce an arrest in the G2 phase of the cell cycle, and to lead to a delayed effect (delayed induction of apoptosis) as compared to etoposide. Measurements have shown that cells exit the G2 phase after at a later stage, at which apoptosis is induced. In the case of etoposide, apoptosis is complete after 48 h, as compared to 120 h in the case of CAP7.1 (a compound of formula (I)).

This delayed apoptosis is likely a reason for a better tolerability and/or safety in the administration of the compounds of formula (I), in particular CAP7.1, as compared to etoposide, because an acutely toxic peak is avoided. Compounds of formula (I), particularly CAP7.1, have been shown to cause fewer side effects than etoposide in preclinical and clinical studies. The compounds of formula (I) are effective in the inhibition of topoisomerase II. They inhibit topoisomerase II enzymes including topoisomerase II a and topoisomerase II [beta] at the transcriptional level. In a preferred embodiment, the present invention relates to a compound of formula (I) as defined above for the treatment of a patient having a tumour that is metastatis and/or that reduces an organ function, wherein the tumour expresses CES1 and/or CES2. Preferably, in this embodiment the fraction of tumour cells that express CES1 and/or CES2 is 50% or higher, more preferably 75% or higher.

Yet another preferred embodiment relates to a treatment wherein the treatment in accordance with the invention further comprises the administration of additional anticancer drugs. The second drug is preferably a protein or a chemotherapeutic drug. The combination therapy preferably involves the simultaneous or sequential administration of the compound of formula (I) and the second drug. The second drug is preferably selected from the group consisting of therapeutic antibodies, kinases, alkylating agents, platinum-based agents, intercalating agents, antibiotics, inhibitors of mitosis, taxanes, inhibitors of topoisomerase and antimetabolites. A preferred second drug is selected from the group consisting of all-trans retinoic acid, azacitide, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, trofosfamide, valrubicin, vinblastine, vincristine, vindesine and vinorelbine. Particularly preferred is carboplatin.

In the context of the herein described invention the term "patient" shall refer to animals or humans. Preferably an animal patient is a mammal, more preferably a farm animal, such as bovine animals, horses, chicken, pigs, cheep, goats etc., or a pet animal such as dogs, cats, birds, rodents etc. Most preferably the patient is a human patient.

Another aspect of the present invention then pertains to a method of inhibiting and/or preventing the growth and/or survival of cancer stem cells. This method can be an in-vitro method, or an in-vivo method, in particular a method of treating a patient suffering from a cancer disease, comprising the administration to said patient of a therapeutically effective amount of a compound described herein above in accordance with the present invention.

Preferably, the method according to the invention includes that the cancer disease is selected from the group consisting drug resistant cancer, a metastatic cancer, an aggressive cancer, a refractory cancer, a recurrent cancer or a non-resectable tumor.

Further preferred is that the patient is suffering from a cancer selected from the group consisting of solid or hematopoietic tumors e.g adenocarci-noma, hypopharynx cancer, lung cancer, diffuse large cell lymphoma, Burkitt's lym-phoma, Hodgkin lymphoma, Non-Hodgkin lymphoma, histiocytic lymphoma, lym-phatic lymphoma, acute T-cell leukaemia, pre-B-acute lymphoblastic leukaemia, chronic and acure myeloitic leukemia, Gastrointestinal cancers eg. (gall bladder-, stomach-, esophageal-, pancreatic-, colon cancer, bile duct carcinoma) thymus carci-noma, urothelium carcinoma, testicular cancer, prostate cancer, bladder cancer, brain tumour, skin tumor including AIDS-related Kaposi's sarcoma, Ewing sarcoma, rhabdomyosarcoma, neuroblastoma, ovarian cancer, melanoma, head and neck cancer, osteosarcoma, breast cancer and CUP syndrome. Most preferred is a method of treatment, wherein the patient after being subject to at least one therapy of said cancer disease is subsequently suffering from a cancer relapse of the same cancer disease.

A method according to the invention of treating, delaying the progression of, preventing a relapse of, alleviating a symptom of, or otherwise ameliorating a human, mammal, or animal subject afflicted with a cancer can include administering a therapeutically effective amount of the compound, product and/or pharmaceutical composition, so that anti-cancer activity occurs. For example, the anti-cancer activity can include slowing the volume growth of the cancer stem cells, stopping the volume growth of the cancer stem cells, or decreasing the volume of the cancer stem cells. The cancer therefore is preferably a cancer characterized by the presence of cancer stem cells. Such cancers can include a solid tumor, a malignancy or a metastatic cell. The cancer can include a carcinoma, a sarcoma, an adenocarcinoma, a lymphoma, or a hematological malignancy. The cancer can be refractory to treatment by chemotherapy, radiotherapy, and/or hormone therapy. The compound, product and/or pharmaceutical composition can be administered to prevent relapse of the cancer. The compound, product and/or pharmaceutical composition can be administered as an adjuvant therapy to surgical resection. The compound, product and/or pharmaceutical composition can be administered, for example, orally and/or intravenously.

A method according to the invention also includes treating, delaying the progression of, preventing a relapse of, alleviating a symptom of, or otherwise ameliorating a disease or disorder in a human, mammal, or animal subject afflicted with that disease or disorder. In some embodiments, the disease or disorder is selected from the group consisting of an autoimmune disease, an inflammatory disease, inflammatory bowel diseases, arthritis, autoimmune demyelination disorder, Alzheimer's disease, stroke, ischemia reperfusion injury and multiple sclerosis.

Administration of the compounds, products and/or pharmaceutical compositions to a patient suffering from a disease or disorder is considered successful if any of a variety of laboratory or clinical results is achieved. For example, administration is considered successful one or more of the symptoms associated with the disease or disorder is alleviated, reduced, inhibited or does not progress to a further, i.e., worse, state. Administration is considered successful if the disorder, e.g., an autoimmune disorder, enters remission or does not progress to a further, i.e., worse, state. Preferably in context of the herein described invention a successful treatment is achieved when the amount, number, or rate of proliferation of the cancer stem cell sub-population in a patient is reduced or dampened. Such a result provides for a better chance of the treated patient to avoid cancer relapse after treatment or the formation of further metastasis.

In some embodiments, the compounds, products and/or pharmaceutical compositions described herein are administered in combination with any of a variety of known therapeutics, including for example, chemotherapeutic and other anti-neoplastic agents, anti-inflammatory compounds and/or immunosuppressive compounds. In some embodiments, the compounds, products and/or pharmaceutical compositions described herein are useful in conjunction with any of a variety of known treatments including, by way of non-limiting example, surgical treatments and methods, radiation therapy, chemotherapy and/or hormone or other endocrinerelated treatment.

These "co-therapies" can be administered sequentially or concurrently. The compounds, products and/or pharmaceutical compositions described herein and the second therapy can be administered to a subject, preferably a human subject, in the same pharmaceutical composition. Alternatively, the compounds, products and/or pharmaceutical compositions described herein and the second therapy can be administered concurrently, separately or sequentially to a subject in separate pharmaceutical compositions. The compounds, products and/or pharmaceutical compositions described herein and the second therapy may be administered to a subject by the same or different routes of administration. In some embodiments, the co-therapies of the invention comprise an effective amount of the compounds, products and/or pharmaceutical compositions described herein and an effective amount of at least one other therapy (e.g., prophylactic or therapeutic agent) which has a different mechanism of action than the compounds, products and/or pharmaceutical compositions described herein. In some embodiments, the co-therapies of the present invention improve the prophylactic or therapeutic effect of the compounds, products and/or pharmaceutical compositions described herein and of the second therapy by functioning together to have an additive or synergistic effect. In certain embodiments, the co-therapies of the present invention reduce the side effects associated with the second therapy (e.g., prophylactic or therapeutic agents).

In some embodiments, the disease or disorder can be treated by administering the compound, product and/or pharmaceutical composition as follows. The blood molar concentration of the compound can be at least an effective concentration and less than a harmful concentration for a first continuous time period that is at least as long as an effective time period and shorter than a harmful time period. The blood molar concentration can be less than the effective concentration after the first continuous time period. For example, the effective concentration can be about 0.1 µM, about 0.2 µM, about 0.5 µM, about 1 µM, about 2 µM, about 3 µM, about 4 µM, about 5 µM, about 6 µM, about 10 µM, or another concentration determined to be effective by one of skill in the art. For example, the harmful concentration can be about 1 µM, about 3 µM, about 10 µM, about 15 µM, about 30 µM, about 100 µM, or another concentration determined to be harmful by one of skill in the art. For example, the effective time period can be about 1 hour, 2 hour, about 4 hours, about 6 hours, about 8 hours, about 10 hours, about 12 hours, about 24 hours, or another time period determined to be effective by one of skill in the art. For example, the harmful time period can be about 12 hours, about 24 hours, about 48 hours, about 72 hours, about 144 hours, or another time period determined to be harmful by one of skill in the art.

In some embodiments, the therapeutically effective amount of the compound, product and/or pharmaceutical composition is selected to produce a blood concentration greater than the $IC_{50}$ of cells of the tumor and less than the $IC_{50}$ of normal cells. In some embodiments, the therapeutically effective amount is selected to produce a blood concentration sufficiently high to kill cells of the tumor and less than the $IC_{50}$ of normal cells.

In some embodiments, the compound, product and/or pharmaceutical composition is administered orally in a dosage form, for example, a tablet, pill, capsule (hard or soft), caplet, powder, granule, suspension, solution, gel, cachet, troche, lozenge, syrup, elixir, emulsion, oil-in-water emulsion, water-in-oil emulsion, and/or a draught.

Another aspect of the present invention then pertains to a pharmaceutical composition comprising a compound of formula (I) as defined above, and optionally a second drug. The above statements regarding the second drug apply accordingly. The pharmaceutical composition preferably comprises further one or more pharmaceutically acceptable carriers and/or excipients.

The pharmaceutical compositions and compounds for use according to the present invention may be formulated for oral, buccal, parenteral, topical, and rectal or transdermal administration, or in a form suitable for administration by inhalation or insulation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions and compounds may take the form of tablets or lozenges formulated in a conventional manner.

The pharmaceutical compositions and compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The pharmaceutical compositions and compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The pharmaceutical compositions and compounds according to the present invention may also be formulated in rectal compositions such as suppositories or retention enemas, e.g. containing conventional suppository bases such as cocoa butter or other glycerides.

In addition to the formulations described previously, the pharmaceutical compositions of the invention may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as emulsion in an acceptable oil) or ion exchange resins or as sparingly soluble derivatives, for example, as a sparingly soluble salt.

The present invention will now be further described in the following examples with reference to the accompanying FIGURES and sequences, nevertheless, without being limited thereto. For the purposes of the present invention, all references as cited herein are incorporated by reference in their entireties.

FIG. 1: shows a cell viability assay using Cap7.1 to inhibit tumor stem cell growth. The effect is tested in cancer stem cells obtained from various solid tumors. Shown are breast cancer stem cells, colon carcinoma stem cells, ovarian cancer stem cells, prostate cancer stem cells and glioblastoma cancer stem cells.

EXAMPLES

The compound CAP7.1 was suspected to have strong inhibitory effects against the growth and survival of various cancer stem cell lines. To this effect, multiple cancer stem cell lines were cultured in the presence of CAP7.1. Thereafter the growth and survival of the cancer stem cells was observed and compared to a control experiment.

As a result of the experiment a surprisingly significant reduction in the survival or growth of cancer stem cell lines was observed. $IC_{50}$ values were determined to be below 20 µM, in most cases even below 10 or 5 µM. Hence, the compound in accordance with the present invention is a strong and selective inhibitor of cancer stem cells of various cancer tissue origin (FIG. 1).

Included in the experiments of the invention were cancer stem cells derived from various breast cancers, colorectal cancer, ovarian cancer, colon cancer, prostatic carcinoma, glioblastoma, and pancreatic carcinoma.

The invention claimed is:
1. A method of inhibiting the growth and/or survival of cancer stem cells in a patient suffering from a cancer disease, comprising the steps of:
  measuring on cancer cells of said patient an expression level of at least one cancer stem cell marker selected from CD19, CD20, CD24, CD26, CD29, CD34, CD38, CD44, CD45, CD105, CD123, CD133, CD166, Stro-1, nestin, GFAP, β-tubulin, CXCR4, α2β1, Oct3, Oct4, Cx43, Lrg5, ABCB5, ABCG2, ALDH, Sca-1 nuclear-catenin, and c-Met; and,
  if the cancer cells of the patient express the at least one cancer stem cell marker at a predetermined level, administering to said patient a therapeutically effective amount of a compound according to formula I,

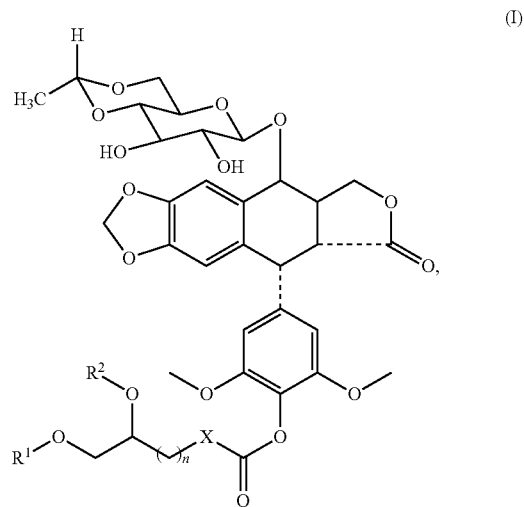

(I)

wherein X is selected from the group consisting of O, NH and S, n is 0, 1 or 2, and $R^1$ and $R^2$ are independently selected from the group consisting of H, methyl and ethyl, or together form a group $CR^3R^4$ and wherein $R^3$ and $R^4$ are independently selected from the group consisting of H, methyl and ethyl, or a solvate or salt thereof.

2. The method according to claim 1, wherein the cancer disease is selected from the group consisting drug resistant cancers, metastatic cancers, aggressive cancers, refractory cancers, recurrent cancers and non-resectable tumors.

3. The method according to claim 1, wherein the patient is suffering from a cancer selected from the group consisting of adenocarcinoma, hypopharynx cancer, lung cancer, diffuse large cell lymphoma, Burkitt's lymphoma, Hodgkin lymphoma, Non-Hodgkin lymphoma, histiocytic lymphoma, lymphatic lymphoma, acute T-cell leukaemia, pre-B-acute lymphoblastic leukaemia, chronic and acute myelo-itic leukemia, gastrointestinal cancers, thymus carcinoma, urothelium carcinoma, testicular cancer, prostate cancer, bladder cancer, brain tumour, skin tumor, Ewing sarcoma, rhabdomyosarcoma, neuroblastoma, ovarian cancer, head and neck cancer, osteosarcoma, melanoma, breast cancer and CUP syndrome.

4. The method according to claim 1, wherein the patient after being subjected to at least one therapy of said cancer disease is subsequently suffering from a cancer relapse of the same cancer disease.

5. The method, according to claim 1, wherein the compound according to formula I is selected from the group consisting of:

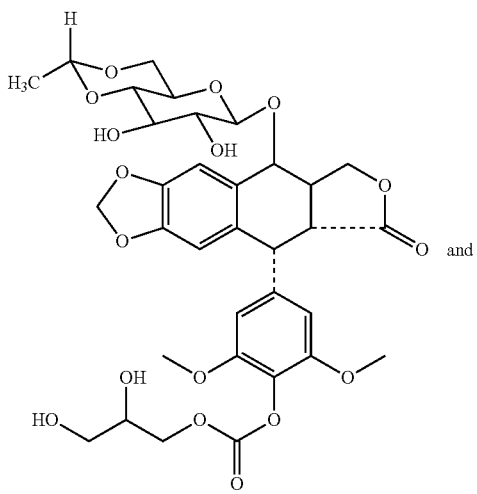 and

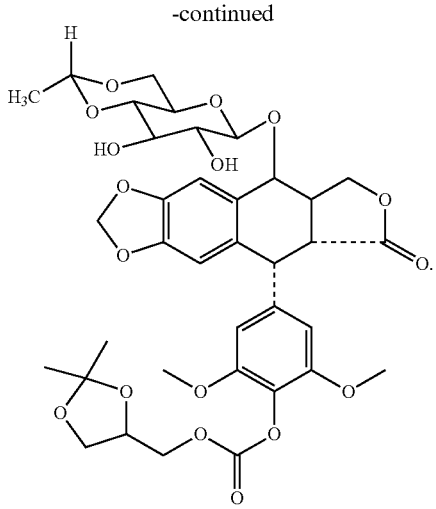

6. The method, according to claim 2, wherein said drug resistant cancer disease is characterized by a tumor expressing a protein of the multi-drug resistant ABC transporter type.

7. The method, according to claim 6, used to treat a tumor having a MDR1 phenotype.

8. The method, according to claim 1, wherein said treatment further comprises the administration of an additional anti-cancer drug.

9. The method, according to claim 1, wherein the patient is a human.

\* \* \* \* \*